(12) United States Patent
Yan et al.

(10) Patent No.: US 8,532,940 B2
(45) Date of Patent: Sep. 10, 2013

(54) SYSTEMS AND METHODS FOR THE INSPECTION OF STRUCTURES HAVING UNKNOWN PROPERTIES

(75) Inventors: Fei Yan, State College, PA (US); Joseph L. Rose, State College, PA (US)

(73) Assignee: FBS, Inc., State College, PA (US)

( * ) Notice: Subject to any disclaimer, the term of this patent is extended or adjusted under 35 U.S.C. 154(b) by 474 days.

(21) Appl. No.: 12/708,183

(22) Filed: Feb. 18, 2010

(65) Prior Publication Data
US 2010/0217544 A1   Aug. 26, 2010

Related U.S. Application Data

(60) Provisional application No. 61/153,526, filed on Feb. 18, 2009.

(51) Int. Cl.
*G01B 5/28* (2006.01)
*G01N 29/07* (2006.01)

(52) U.S. Cl.
CPC .................................... *G01N 29/07* (2013.01)
USPC ................. 702/36; 702/35; 702/39; 702/56

(58) Field of Classification Search
CPC ............................................ G01N 2291/0289
USPC ............................................ 702/36, 39, 103
See application file for complete search history.

(56) References Cited

U.S. PATENT DOCUMENTS

| | | | | |
|---|---|---|---|---|
| 3,693,415 | A * | 9/1972 | Whittington | 73/619 |
| 4,155,260 | A * | 5/1979 | Engeler et al. | 73/626 |
| 4,307,612 | A * | 12/1981 | Elsley et al. | 73/613 |
| 4,522,064 | A * | 6/1985 | McMillan | 73/592 |
| 4,523,468 | A * | 6/1985 | Derkacs et al. | 73/598 |
| 5,629,485 | A * | 5/1997 | Rose et al. | 73/599 |
| 5,734,588 | A * | 3/1998 | Rose et al. | 702/39 |
| 2004/0255678 | A1* | 12/2004 | Nagashima et al. | 73/620 |
| 2005/0075570 | A1* | 4/2005 | Shinomura et al. | 600/459 |
| 2005/0228597 | A1* | 10/2005 | Giurgiutiu et al. | 702/35 |
| 2005/0268720 | A1* | 12/2005 | Quarry | 73/627 |
| 2008/0110266 | A1* | 5/2008 | Randall et al. | 73/661 |
| 2008/0190205 | A1* | 8/2008 | Messer et al. | 73/592 |
| 2008/0314153 | A1* | 12/2008 | Langlois et al. | 73/606 |
| 2009/0084184 | A1* | 4/2009 | Dijkstra et al. | 73/623 |

OTHER PUBLICATIONS

Shin et al., Guided Wave Tuning Principles for Defect Detection in Tubing, Journal of Nondestructive Evaluation, vol. 17, No. 1, 1998.*
Joseph L. Rose, "Ultrasonic Waves in Solid Media", The Pennsylvania State University, Cambridge University Press 1999, ISBN 0 521 64043 1.
Giurgiutiu, V. (2005) "Tuned Lamb-Wave Excitation and Detection with Piezoelectric Wafer Active Sensors for Structural Health Monitoring", Journal of Intelligent Material Systems and Structures, vol. 16, No. 4, pp. 291-306, Apr. 2005.

* cited by examiner

*Primary Examiner* — Sujoy Kundu
*Assistant Examiner* — Timothy H Hwang
(74) *Attorney, Agent, or Firm* — Duane Morris LLP

(57) ABSTRACT

An inspection method includes driving a plurality of spaced apart transmitting transducer elements with a respective time delay and a respective frequency such that each of the transmitting transducer elements transmits an ultrasonic guided wave through a transmission medium defined by a material having at least one unknown physical property. The ultrasonic guided waves are received at a receiving transducer element disposed at a distance from the transmitting transducer elements. A respective time delay and a respective frequency for each of the transmitting transducer elements is determined that provides a maximum amplitude in a signal received at the receiving transducer element. The plurality of transmitting transducer elements are activated in accordance with the determined time delays and frequencies to transmit inspection signals through the transmission medium. A location of a defect in the material is determined based on velocities of the inspection signals received at the receiving transducer element.

17 Claims, 15 Drawing Sheets

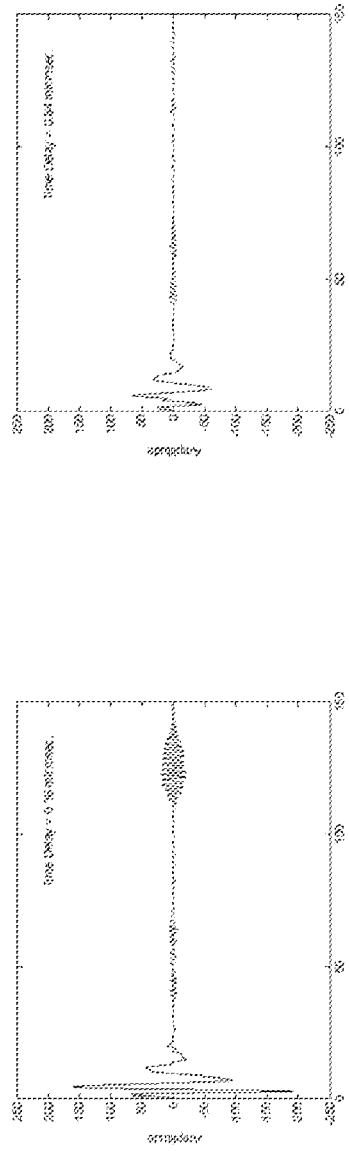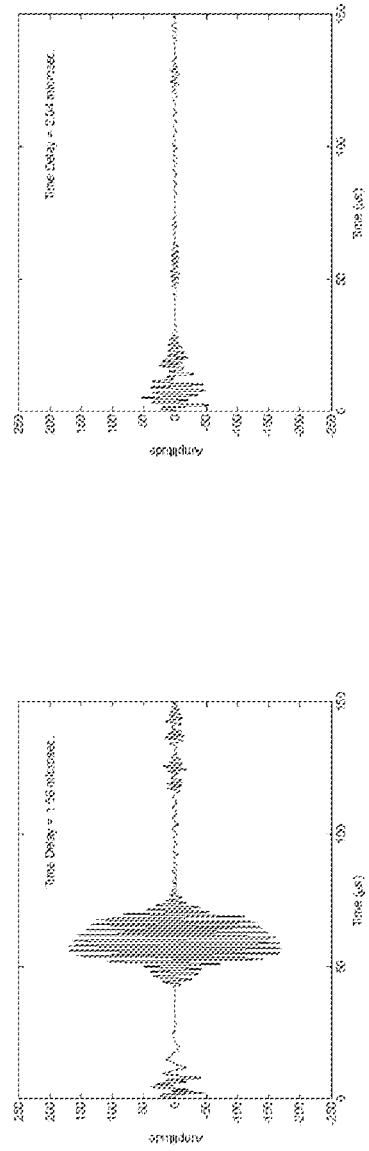
FIG. 11A
FIG. 11B
FIG. 11C
FIG. 11D

SYSTEMS AND METHODS FOR THE INSPECTION OF STRUCTURES HAVING UNKNOWN PROPERTIES

CROSS-REFERENCE TO RELATED APPLICATIONS

This application claims priority to U.S. Provisional Patent Application Ser. No. 61/153,526, which was filed on Feb. 18, 2009, the entirety of which is herein incorporated by reference.

FIELD OF DISCLOSURE

The disclosed systems and methods relate to nondestructive evaluations (NDE) and structural health monitoring (SHM) of structures with unknown properties. More specifically, the disclosed systems and methods relate to defect detection in both isotropic and anisotropic structures with unknown material properties and/or unknown exact geometry dimensions.

BACKGROUND

Ultrasonic NDE and SHM methods serve as one of the primary maintenance techniques to ensure the safe operations of various mechanical structures, such as aircraft structures, pipelines, ships, and railways. With reliable defect detection capabilities, ultrasonic NDE and SHM methods are extensively used in the field to determine whether the inspected structures need to be repaired or replaced to ensure structural safety.

In ultrasonic NDE and SHM, quite often it is encountered some inspection objects, whose material properties and accurate dimensions are unknown due to poor records, material degradations, or other reasons. Conventional ultrasonic inspection techniques are problematic because the inspections rely on the ultrasonic wave speeds that are usually calculated from the material properties. For structures with material anisotropies, for instance, fiber-reinforced composite structures, it is also critical to know the direction dependence of the wave speeds. Furthermore, ultrasonic guided wave inspection techniques usually require the generation of guided wave dispersion curves based on the material properties as well as the geometries of the structures to be inspected. Dispersion curves not only serve as guidelines for selecting the parameters of the transducers that are suitable for the ultrasonic inspections, but also play an important role in determining the defect locations. When applying conventional ultrasonic guided wave techniques to inspect anisotropic structures, the directionally dependant dispersion curves and the direction of anisotropy need to be known. Similar requirements on the knowledge of wave velocities from the material properties and structure geometries are applied to passive acoustic emission tests, in which the location of the acoustic emission source, i.e., the defect location, is determined on the basis of the time-of-flights (TOFs) of the acoustic emission signals and the corresponding wave speeds. Consequently, conventional systems and methods do not allow for the inspection of materials having unknown properties such as the direction of anisotropy.

Accordingly, a system and method for inspecting a material having unknown properties is desirable.

SUMMARY

An inspection system is disclosed including a plurality of spaced apart transmitting transducer elements for coupling to a surface of a material defining a transmission medium and having at least one unknown physical property. Each of the transmitting transducers is configured to transmit ultrasonic guided waves through the transmission medium. A receiving transducer element for coupling to the surface of the material is configured to receive ultrasonic guided wave signals through the transmission medium. A control and processing device is in signal communication with each of the transducer elements. The control and processing device includes a computer readable storage medium configured to store a plurality of time delays for applying to each of the transducer elements and a processor in signal communication with the computer readable storage medium. The processor is configured to apply the time delays and a driving frequency to the transmitting transducer elements, determine a respective time delay and frequency for each of the transmitting transducer elements that provides a maximum amplitude in a signal received at the receiving transducer element, activate each of the plurality of transmitting transducer elements in accordance with the determined time delay and frequency to transmit an inspection signal through the transmission medium, and determine a location of a defect in the material based on a velocity of the inspection signal received at the receiving transducer element.

An inspection method is disclosed in which each of a plurality of spaced apart transmitting transducer elements are driven with a respective time delay and a respective frequency such that each of the transmitting transducer elements transmits an ultrasonic guided wave through a transmission medium defined by a material having at least one unknown physical property. The ultrasonic guided waves are received at a receiving transducer element disposed on the surface of the material at a distance from the transmitting transducer elements. A respective time delay and a respective frequency for each of the transmitting transducer elements is determined that provides a maximum amplitude in a signal received at the receiving transducer element. Each of the plurality of transmitting transducer elements are activated in accordance with the determined time delays and frequencies to transmit inspection signals through the transmission medium. A location of a defect in the material is determined based on velocities of the inspection signals received at the receiving transducer element.

A computer readable storage medium is also disclosed. The computer readable storage medium is encoded with program code, wherein when the program code is executed by a processor, the processor performs a method. The method includes driving each of a plurality of spaced apart transmitting transducer elements with a respective time delay and a respective frequency such that each of the transmitting transducer elements transmits an ultrasonic guided wave through a transmission medium defined by a material having at least one unknown physical property; receiving the ultrasonic guided waves at a receiving transducer element disposed on the surface of the material at a distance from the transmitting transducer elements, and determining a respective time delay and a respective frequency for each of the transmitting transducer elements that provides a maximum amplitude in a signal received at the receiving transducer element. Each of the plurality of transmitting transducer elements are activated in accordance with the determined time delays and frequencies to transmit inspection signals through the transmission medium, and a location of a defect in the material is determined based on velocities of the inspection signals received at the receiving transducer element.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIGS. 11A-11D are experimental signals obtained by using different time delays on a comb type transducer;

DETAILED DESCRIPTION

The disclosed systems and methods provide for detecting, locating, and evaluating defects in isotropic and anisotropic structures with unknown properties and/or exact geometry dimensions in a wide range of materials and structural geometries. Long range inspections may be performed through the use of ultrasonic guided waves and acoustic emissions. The systems and methods disclosed herein provide low cost and easy to implement through the use of acoustic emissions for structural health monitoring (SHM) applications.

Figure 1:
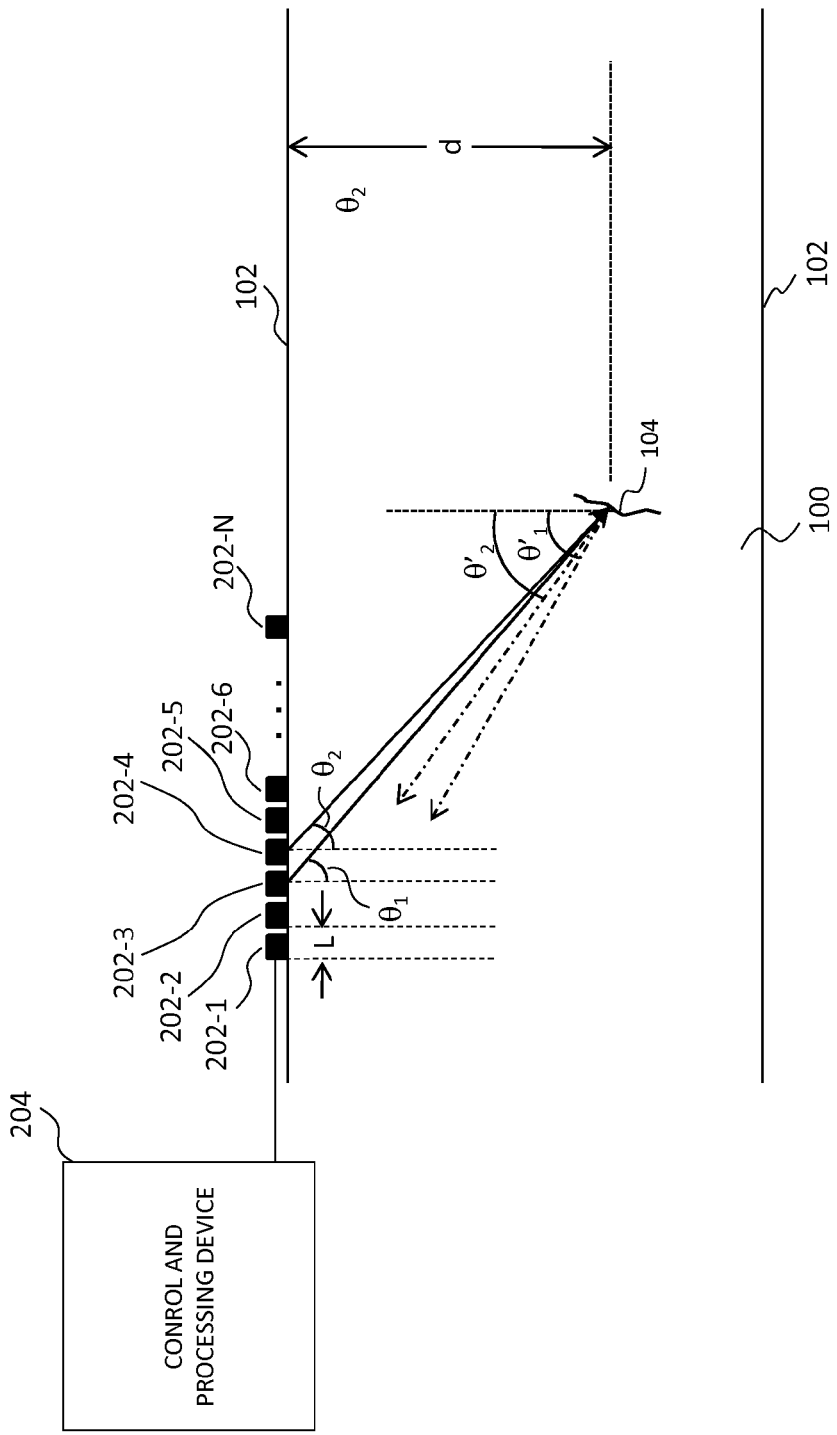
FIG. 1 is a cross-sectional view of one example of a system for inspecting a material having unknown properties using ultrasonic bulk waves.

FIG. 1 illustrates one example of an apparatus for the inspection of an object 100 using a bulk wave phased array. The system includes a plurality of transducer elements 202 disposed on a surface 102 of the object 100, which may be an isotropic material 100. Transducer elements 202, such as, for example, a piezoelectric transducer, are capable of transmitting and receiving ultrasonic bulk waves in the material 100.

Figure 2:
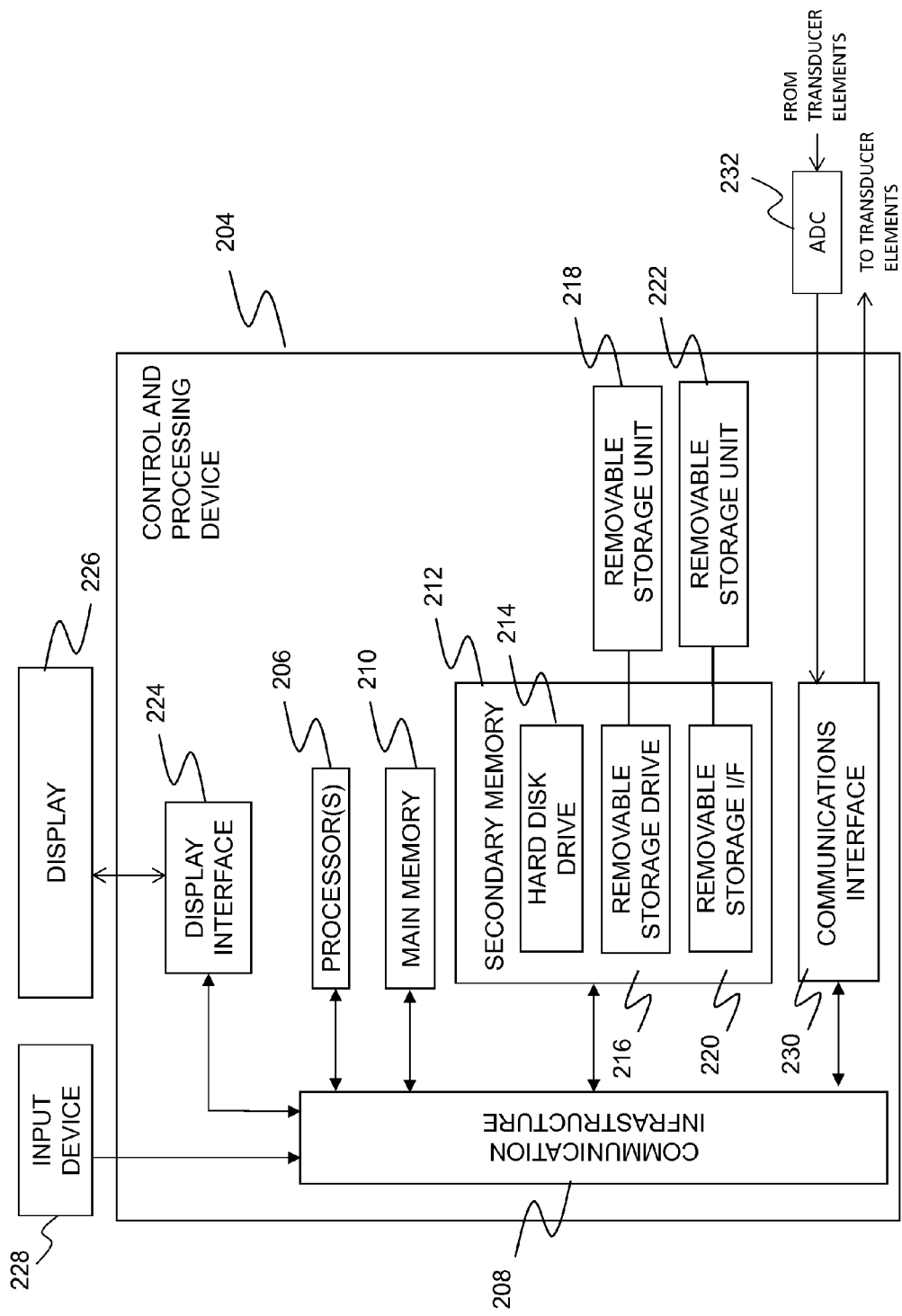
FIG. 2 is a block diagram of one example of an architecture of a control and processing device.

Transducer elements 202 are coupled to a control and processing device 204, which may be a computer. As shown in FIG. 2, the computer system 204 may include one or more processors, such as processor(s) 206. Processor(s) 206 may be any central processing unit (CPU), microprocessor, microcontroller, or computational device or circuit for executing instructions and be connected to a communication infrastructure 208 (e.g., a communications bus, cross-over bar, or network). Various software embodiments are described in terms of this exemplary computer system. After reading this description, it will be apparent to one skilled in the art how to implement the method using other computer systems or architectures.

Computer system also includes a main memory 210, such as a random access (RAM) memory, and may also include a secondary memory 212. The secondary memory 212 may include a more persistent memory such as, for example, a hard disk drive 214 and/or removable storage drive 216, representing a floppy disk drive, a magnetic tape drive, an optical disk drive, or the like. The removable storage drive 216 reads from and/or writes to a removable storage unit 218 in a manner that is understood by one skilled in the art. Removable storage unit 218 represents a floppy disk, magnetic tape, optical disk, or the like, which may be read by and written to by removable storage drive 216. As will be understood by one skilled in the art, the removable storage unit 218 may include a computer usable storage medium having stored therein computer software and/or data.

In some embodiments, secondary memory 212 may include other devices for allowing computer programs or other instructions to be loaded into computer system 204. Such devices may include, for example, a removable storage unit 222 and a corresponding interface 220. Examples of such units 222 and interfaces 220 may include a program cartridge and cartridge interface (such as that found in video game devices), a removable memory chip (such as an erasable programmable read only memory (EPROM)), or programmable read only memory (PROM)) and associated socket, and other removable storage units 222 and interfaces 220, which allow software and data to be transferred from the removable storage unit 222 to computer system 204.

Computer system 204 may include a display interface 224 that forwards graphics, text, and other data from the communication infrastructure 208 (or from a frame buffer not shown) for display on a monitor or display unit 226. An input device 228 may also be coupled to the communication infrastructure 208 enabling a user to input instructions or data to computer system 204. Examples of input device 228 include, but are not limited to, a mouse, a keyboard, a touch screen, a track ball, a microphone, and a camera, to name a few.

Computer system 204 may also include a communications interface 230, which allows software and data to be transferred between computer system 204 and external devices such as, for example, an analog-to-digital converter (ADC) 232 and transducer elements 202. Examples of communications interface 230 may include, without limitation, a modem, a network interface (such as an Ethernet card), a communications port, a Personal Computer Memory Card International Association (PCMCIA) slot and card, or any combination thereof. Software and data transferred via communications interface 230 are in the form of signals, which may be electronic, electromagnetic, optical, or other signals capable of being transmitted and received by communications interface 230. These signals are transmitted by communications interface 230 via a communications path or channel. The channel may be implemented using wire or cable, fiber optics, a telephone line, a cellular link, a radio frequency (RF) link, or other communication channels.

ADC 232 may be a single channel ADC or a multichannel ADC as will be understood by one skilled in the art. Additionally, ADC 232 may be separate from control and processing device 204 or integrated in the control and processing device 204.

In this document, the terms "computer program medium" and "computer readable medium" refer to media such as removable storage units 218, 222, or a hard disk installed in hard disk drive 214. These computer program products provide software to computer system 204. Computer programs (also referred to as computer control logic) may be stored in main memory 210 and/or secondary memory 212. Computer programs may also be received via communications interface 230. Such computer programs, when executed by a processor(s) 206, enable the computer system 204 to perform the features of the method discussed herein.

In an embodiment where the method is implemented using software, the software may be stored in a computer program product and loaded into computer system 204 using removable storage drive 216, hard drive 214, or communications interface 230. The software, when executed by a processor(s) 206, causes the processor(s) 206 to perform the functions of the method described herein.

In another embodiment, the method is implemented primarily in hardware using, for example, hardware components such as application specific integrated circuits (ASICs). Implementation of the hardware state machine so as to perform the functions described herein will be understood by persons skilled in the art. In yet another embodiment, the method is implemented using a combination of both hardware and software.

In the embodiment illustrated in FIG. 1, the phased array includes 16 transducer elements 202, e.g., N=16, although one skilled in the art will understand that fewer or more transducer elements may be implemented. The arrayed transducer elements 202 are sequentially grouped into a series of arrays defining an array aperture between adjacent transducer elements 202. For example, the first five transducer elements 202-1:202-5 from the left of the array are grouped as Group 1. With a one transducer element increment, the second to sixth transducer elements 202-2:202-6 from the left of the array are grouped as Group 2. In such an example, a total of (N−4) Groups of transducer elements can be defined. Transducer elements 202 are sequentially activated by control and processing device 204. When time delays are applied to the transducer elements of Group 1, the ultrasonic wave beam is steered into a certain direction, as demonstrated in FIG. 1. The beam steering direction is a function of the ultrasonic wave velocity and an applied time delay schedule, which may be stored in a computer readable storage medium such as, for example, main memory 210 and/or secondary memory 212.

Pulse echo signals are received by control and processing device 204 from each transducer element 202 through multi-channel ADC 232. The received signals contain the defect reflections from possible defects, e.g., defect 104, which may be a crack or other material abnormality in material 100. Once again, different time delay schedules are applied to the received signals from each array transducer element Group. The time delays are synthetically applied in the control and processing device 204 that performs post-processing of the signals. By synthesizing the received signals, the reflected signals may be enhanced if the time delays match the arrival time differences in the signals received by different transducer elements due to the reflection angles. As demonstrated in FIG. 1, the defect reflection direction can be different from the incident beam steering direction due to the shape of defect 104.

Figure 3:
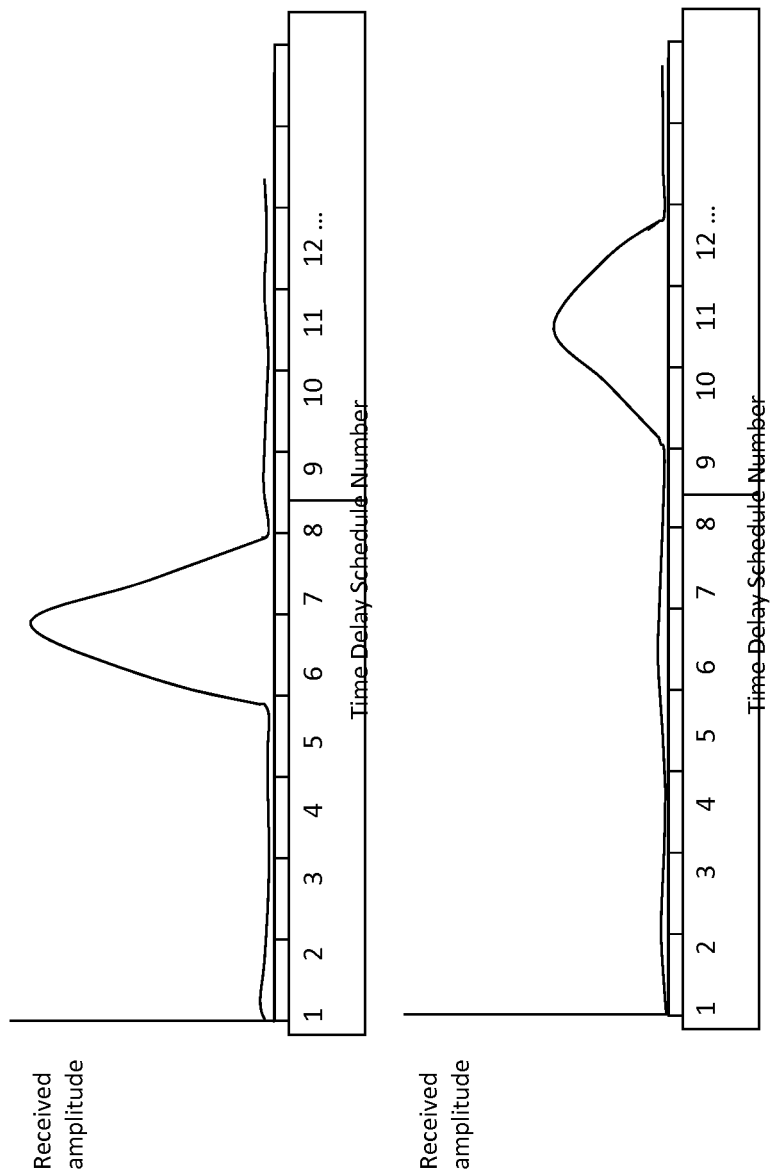
FIG. 3 illustrates differing amplitudes of reflected signals received for different time delay schedules.

Maximum amplitude of the defect reflection can be observed when the time delays agree with the time delays for steering the ultrasonic beam into the direction facing the defect reflection. FIG. 3 illustrates one example of different amplitudes in the synthesized received waveforms when the different time delay schedules are applied to the signals received by transducer elements 202. The material properties of the objects to be inspected are considered unknown. Consequently, there is thus no direct way to determine what the beam steering angle is for a certain time delay schedule. However, a series of time delay schedules can be employed for both the wave transmission and reception to generate a large signal database for the phased array test approach. The signal database may be stored in a computer readable storage medium such as main memory 210 and/or secondary memory 212. Since different time delay schedules cover different wave transmission and reception angles, the signal database produces wide coverage of the object to be inspected. The defect detection process can therefore be conducted without the material properties as long as defect reflections can be observed in the signal database. Furthermore, the optimum time delays for detecting the defect and the optimum time delays for receiving the defect reflection can be determined from the database based on the maximum reflection amplitude.

In the example shown in FIG. 1, the time delays for reception are only applied within the array element Groups. For example, when using Group 1, i.e., transducer elements 202-1:202-5, for the wave transmission, the time delays for reception are only applied to the signals received by the array transducer elements of Group 1. If necessary, the time delays can be applied to all transducer elements of the array to enable a larger array aperture and therefore a wider reception angle range to cover defects 104 with different shapes.

Once a defect 104 is identified from the test approach described above, the next step is to determine the defect location, shape, and size. For a certain defect 104 and transducer element group, there is an optimum incident angle (beam steering angle for transmission) and a corresponding defect reflection angle, for example, the incident angle $\theta_1$ and the defect reflection angle $\theta'_1$ shown in FIG. 1 for transducer element Group 1. The incident and reflection angles $\theta_1, \theta_2$ are measured from an axis that is orthogonal to an axis defined by the surface 102 of the material 100 on which transducer elements 202 are disposed as shown in FIG. 1. Similarly, when Group 2 is used, there are incident angle $\theta_2$ and reflection angle $\theta'_2$, which may be measured from the same reference axis that the incident and reflection angles of Group 1 are measured. The distance between Groups 1 and 2, as shown in FIG. 1, is L. Based on an assumption that a same portion of defect 104 produces the maximum defect reflection amplitudes for the signal databases of Groups 1 and 2, a series of equations can be written as follows:

$$d^*\tan(\theta_1) = d^*\tan(\theta_2) + L \qquad \text{Eq. 1}$$

$$\tau_1 = L^*\sin(\theta_1)/C \qquad \text{Eq. 2}$$

$$\tau_2 = L^*\sin(\theta_2)/C \qquad \text{Eq. 3}$$

$$\tau'_1 = L^*\sin(\theta'_1)/C \qquad \text{Eq. 4}$$

$$\tau'_2 = L^*\sin(\theta'_2)/C \qquad \text{Eq. 5}$$

$$T_1{}^*C = d/\cos(\theta'_1) + d/\cos(\theta_1) \qquad \text{Eq. 6}$$

$$T_2{}^*C = d/\cos(\theta'_2) + d/\cos(\theta_2) \qquad \text{Eq. 7}$$

Where,
  d is the defect depth;
  $\tau_1$ and $\tau_2$ are the time delays for the optimum beam steering angles of Groups 1 and 2, respectively;
  $\tau'_1$ and $\tau'_2$ are the corresponding time delays for the optimum receptions;
  $T_1$ and $T_2$ are the TOFs of the defect echoes in the synthesized reception signals from groups 1 and 2 respectively; and C is the wave velocity.

In the seven equations above, there are six unknowns, i.e., $\theta_1$, $\theta_2$, $\theta'_1$, $\theta'_2$, d, and C, and thus there is an overdetermined system and the unknowns may be calculated. Mathematical methods such as least square method can be used to solve the overdetermined system given by Equations 1-7. A similar process can be applied to different transducer element Groups. For each two Groups, a set of 6 parameters including $\theta_1$, $\theta_2$, $\theta'_1$, $\theta'_2$, d, and C can be solved. Since the wave velocities in the isotropic material 100 are constant for different directions, the values of C should be the same in all calculations.

However, due to the assumption that the defect depth, d, that produces maximum reflection amplitudes for two adjacent array element groups is the same, there can be discrepancies among the C values calculated using different transducer element Group combinations. Consequently, a further calculation process can be applied to reduce the discrepancies in the C values. An example process is to use the averaged value of the velocity C calculated from different group combinations as a known parameter for Equations 1-7 set forth above. The overdetermined system then has 5 unknowns instead of 6. The overdetermined system can be re-evaluated to yield a new set of data for the defect depth, d, the incident angles, $\theta_1$, $\theta_2$, and the defect reflection angles, $\theta'_1$, $\theta'_2$. The defect location, shape, and size can then be analyzed from the new data set. Other more sophisticated methods such as a genetic algorithm can also be applied to minimize the discrepancies among the C values. Once identified, a location, size, and shape of the defect 104 may be stored in a computer readable storage medium 210, 212. Additionally, a rendering of the defect 104 created by the processor 206 may be displayed to a user of the control and processing device 204 on the display 224 as will be understood by one skilled in the art.

Figure 4A:
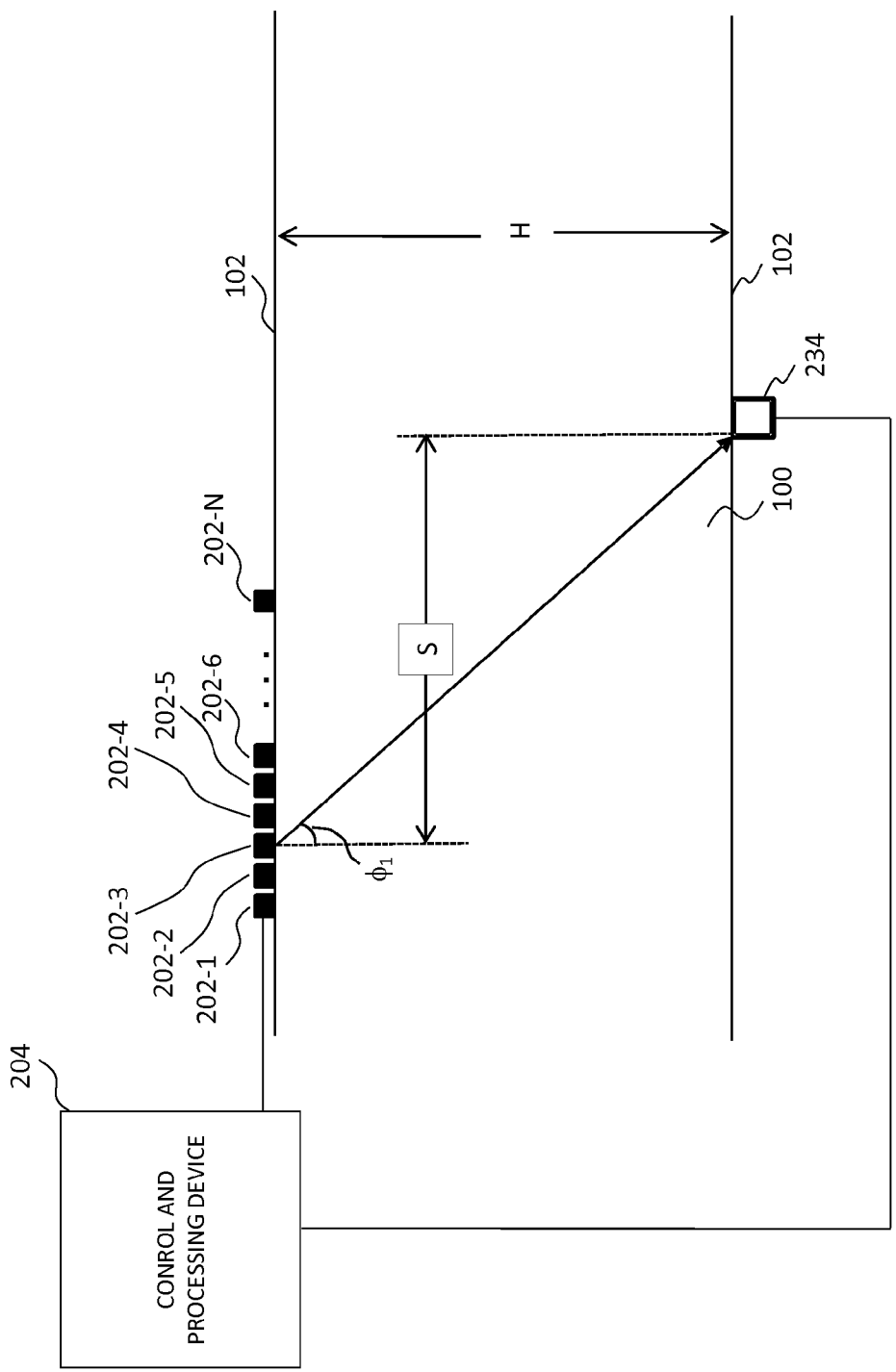
FIG. 4A illustrates one example of a calibration system for a system of inspecting a material having unknown properties.
Figure 4B:
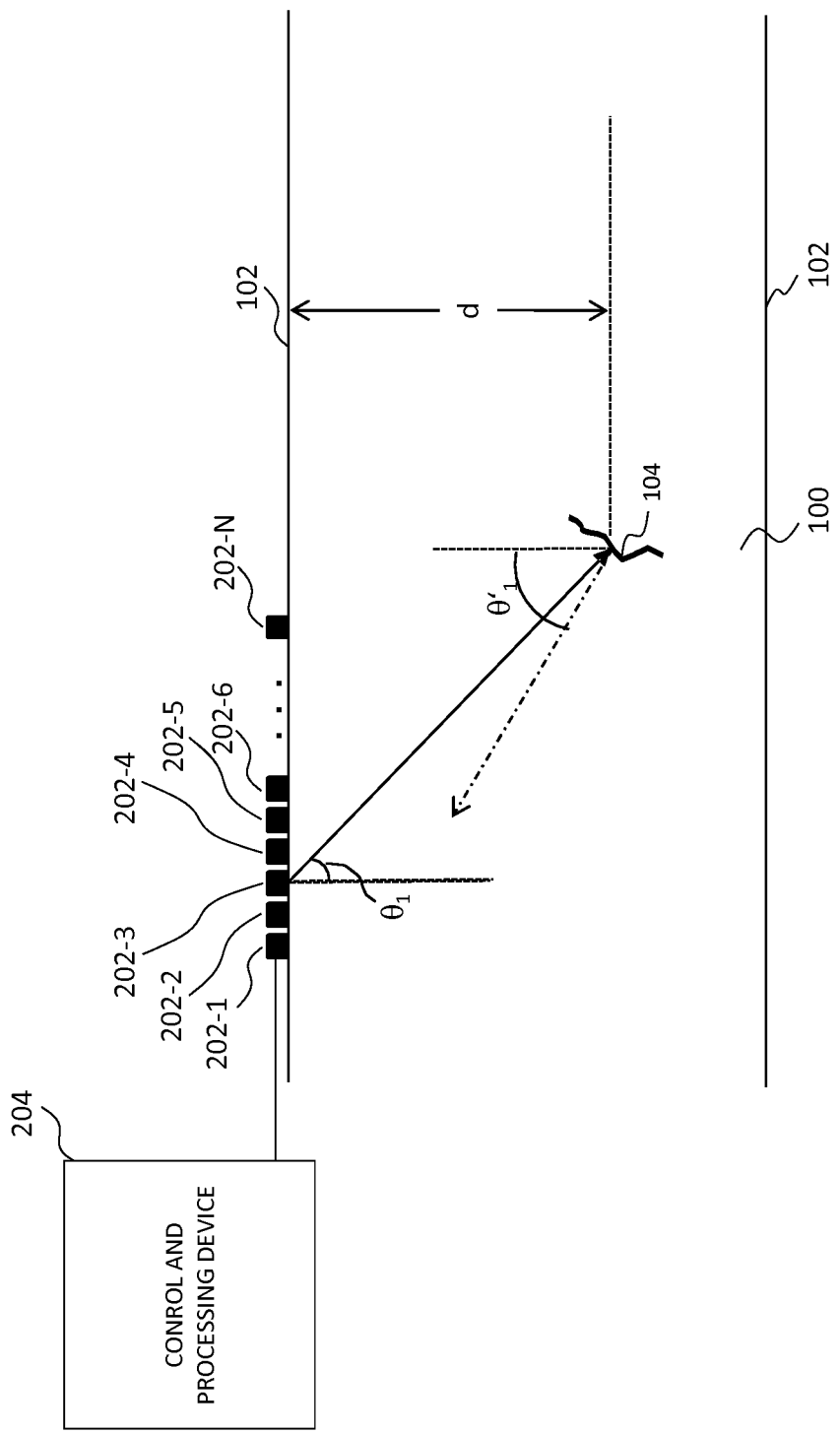
FIG. 4B illustrates another cross-sectional view of an example of a system for inspecting a material having unknown properties.

FIGS. 4A and 4B illustrate the bulk-wave phased-array inspection method applied to inspect an anisotropic object 100 with unknown material properties. For anisotropic materials, a calibration process is implemented. As shown in FIG. 4A, a receiver transducer 234 is placed at a known location with respect to the transducer element array location. Accordingly, the parameters S and H in FIG. 4A are known. The calibration process constructs the energy velocity profile and the time delay schedules with respect to the wave propagation direction due to the fact that wave propagations in anisotropic materials are directionally dependent. Furthermore, because of the wave skew effect introduced by the material anisotropy, the wave energy propagation directions and the energy velocities can be different from the wave launching directions and the corresponding phase velocities. In bulk-wave phased-array applications, the wave launching directions are the beam steering directions determined by the time delays and the phase velocities. The TOFs of defect reflections, by contrast, depend on the energy velocities and the defect locations. For the calibration, different time delay schedules are applied to different array element groups similar to the phased array wave transmissions described above with respect to the isotropic cases. While changing the time delay schedules, the maximum amplitudes of the wave signals are obtained by the receiver transducer when the wave energy directions are from the centers of the array element groups to the receiver position. FIG. 4A illustrates an example of transducer element Group 1. As shown in FIG. 4A, the direction from the center of Group 1 to the receiver transducer 234 yields $\phi_1$ as the energy velocity direction for the reception of the maximum wave amplitude. It should be noticed that the phase velocity direction can be different. Considering the calibration tests for array transducer element Groups 1 and 2, the four following equations can be obtained:

$$C_E(\phi_1)*T_1 = H/\cos(\phi_1) \qquad \text{Eq. 8}$$

$$C_E(\phi_2)*T_2 = H/\cos(\phi_2) \qquad \text{Eq. 9}$$

$$\tan(\phi_1) = S/H \qquad \text{Eq. 10}$$

$$\tan(\phi_2) = (S-L)/H \qquad \text{Eq. 11}$$

Where,
  $C_E(\phi)$ represents the energy velocity at the angle $\phi$ direction.

The TOFs, $T_1$ and $T_2$, are known as are parameters S and H. Accordingly, there are two unknowns, $C_E(\phi_1)$ and $C_E(\phi_2)$, which can be solved using Equation 8-11 set forth above. By using different array transducer element Groups and also by placing the receiver 234 at different positions along the surface 102 of the material 100, an angular dependence of energy velocity, $C_E(\phi)$, can be obtained in the calibration process for a variety of angles. At the same time, the time delays for the maximum received wave amplitudes are also recorded and may be stored in a computer readable storage medium such as main memory 210 and/or secondary memory 212 such that the corresponding applied time delays as a function of the energy velocity directions, $\tau(\phi)$, can be generated.

Referring now to FIG. 4B, the same time delay schedule tuning procedure as described above for the isotropic cases are applied to inspect anisotropic objects after the functions $C_E(\phi)$ and $\phi(\tau)$ are obtained in the calibration process. A different set of equations can be generated based on the signal database obtained with different transmission time delays as well as different reception time delays. The equations are listed as follows:

$$d*\tan(\theta_1) = d*\tan(\theta_2) + L \qquad \text{Eq. 12}$$

$$d*C_E(\theta_1)/\cos(\theta_1) + d*C_E(\theta'_1)/\cos(\theta'_1) = T_1 \qquad \text{Eq. 13}$$

$$d*C_E(\theta_2)/\cos(\theta_2) + d*C_E(\theta'_2)/\cos(\theta'_2) = T_2 \qquad \text{Eq. 14}$$

$$\tau_1 = \tau(\theta_1) \qquad \text{Eq. 15}$$

$$\tau_2 = \tau(\theta_2) \qquad \text{Eq. 16}$$

$$\tau'_1 = \tau(\theta'_1) \qquad \text{Eq. 17}$$

$$\tau'_2 = \tau(\theta'_2) \qquad \text{Eq. 18}$$

Where,
  d is the defect depth, $\theta_1$ and $\theta_2$ are the energy incident angles for the receptions of maximum defect reflections when Groups 1 and 2 are used;
  $\theta'_1$ and $\theta'_2$ are the corresponding energy reflection angles;
  $T_1$ and $T_2$ are the TOFs of the defect reflections with maximum amplitudes;
  $\tau_1$ and $\tau_2$ are the time delays corresponding to the energy incident angles $\theta_1$ and $\theta_2$; and
  $\tau'_1$ and $\tau'_2$ are the time delays for the energy reflection angles $\theta'_1$ and $\theta'_2$.

Among the parameters included in Equations 12-18, $T_1$, $T_2$, $\tau_1$, $\tau_2$, $\tau'_1$ and $\tau'_2$ are all known. $C_E(\phi)$ and $\phi(\tau)$ are available from the calibration process leaving only 5 unknowns, $\theta_1$, $\theta_2$, $\theta'_1$, $\theta'_2$, and d, for the 7 equations, i.e., Equations 12-18. Accordingly, an overdetermined system is obtained and can be solved to provide the defect information for anisotropic objects with unknown material properties. Once identified, a location, size, and shape of the defect 104 may be stored in a computer readable storage medium 210, 212. Additionally, a rendering of the defect 104 created by the processor 206 may be displayed to a user of the control and processing device 204 on the display 224 as will be understood by one skilled in the art.

As described above, there is no specific requirement for the use of the method of least squares to solve the overdetermined systems and any mathematical or numerical method capable of obtaining the unknowns from an overdetermined system are applicable. Genetic algorithm based methods may also be used to solve the overdetermined system as will be understood by one skilled in the art. The redundant nature of the overdetermined system enables the method to be used for inspecting structures having material inhomogeneities.

Figure 5:
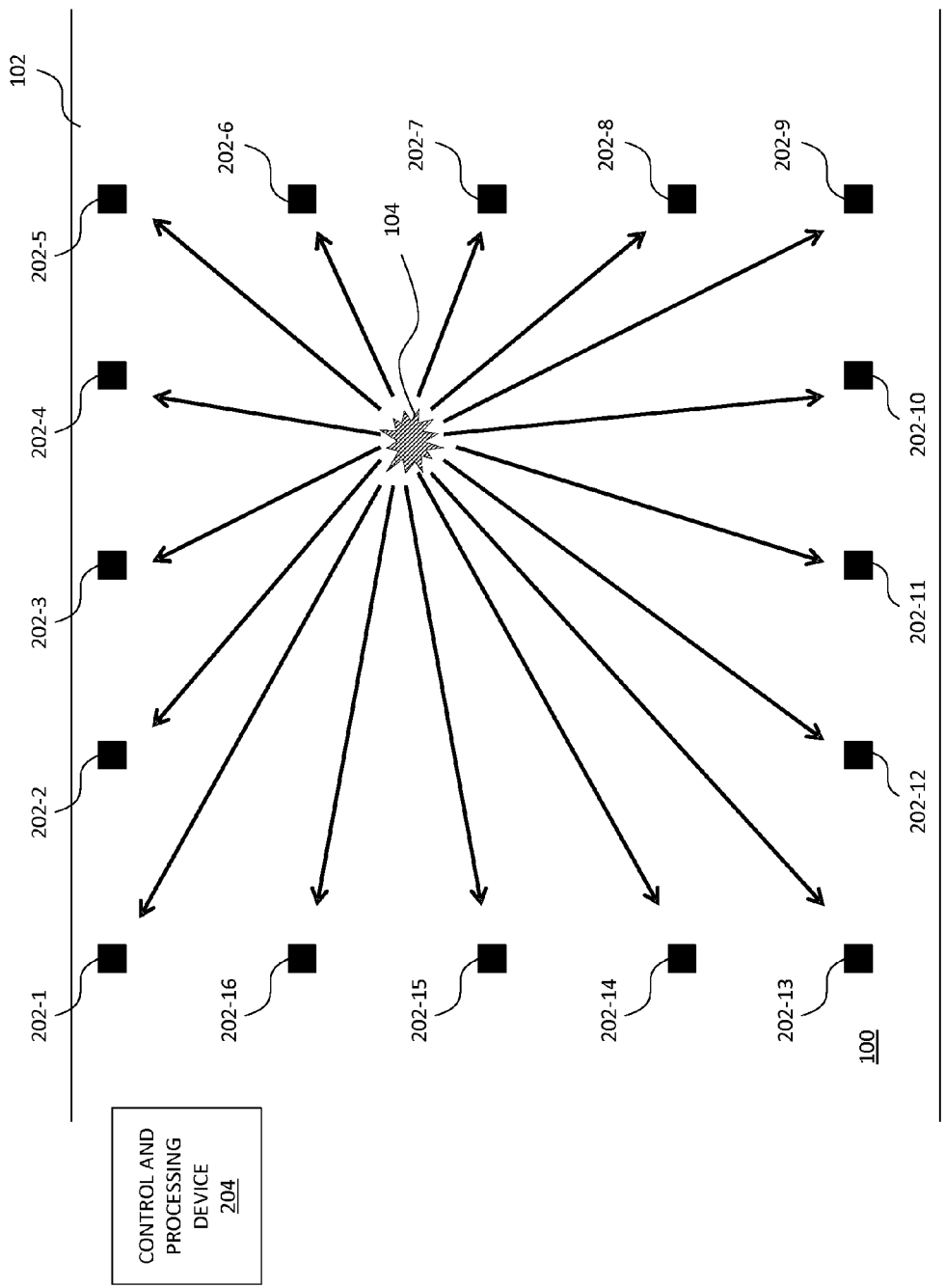
FIG. 5 is a plan view of a system for inspecting a material having unknown properties.

FIG. 5 is a plan view of an example embodiment of an acoustic emission system for detecting damage to a material 100. As shown in FIG. 5, acoustic transducer elements 202-1:202:16 are arranged in a rectangular transducer element network on a surface 102 of a material 100. Each transducer element 202 is coupled to the control and processing device 204 although not shown in FIG. 5. The ultrasonic energy generated by an impact to the material 100 propagates to the transducer elements 202 at different arrival times due to the wave path differences to different transducer elements 202. For anisotropic material, the directional dependence of the energy velocity profile also affects the arrival times of the wave energies received by different transducer elements 202.

Control and processing device 204 may record the arrival times of the ultrasonic energy received at each of the transducer elements 202 in a computer readable storage medium such as main memory 210 or secondary memory 212. Additionally, control and processing device 204 may calculate the difference between the arrival times using one or more processors 206 as will be understood by one skilled in the art. The differences in arrival times may also be stored in a computer readable storage medium 210, 212. The arrival times may be recorded from a triggering event, which may be the impact on the material 100, the first arrival of the ultrasonic energy at a transducer element 202, or other event. If the arrival time of a signal received at a transducer element 202 is used as the trigger event, a time, delta t, is used to approximate the difference between the first arrival and the actual acoustic emission event, i.e., the impact time. If the triggering event is the actual acoustic emission time, then the delta t value will be zero.

Figure 6:
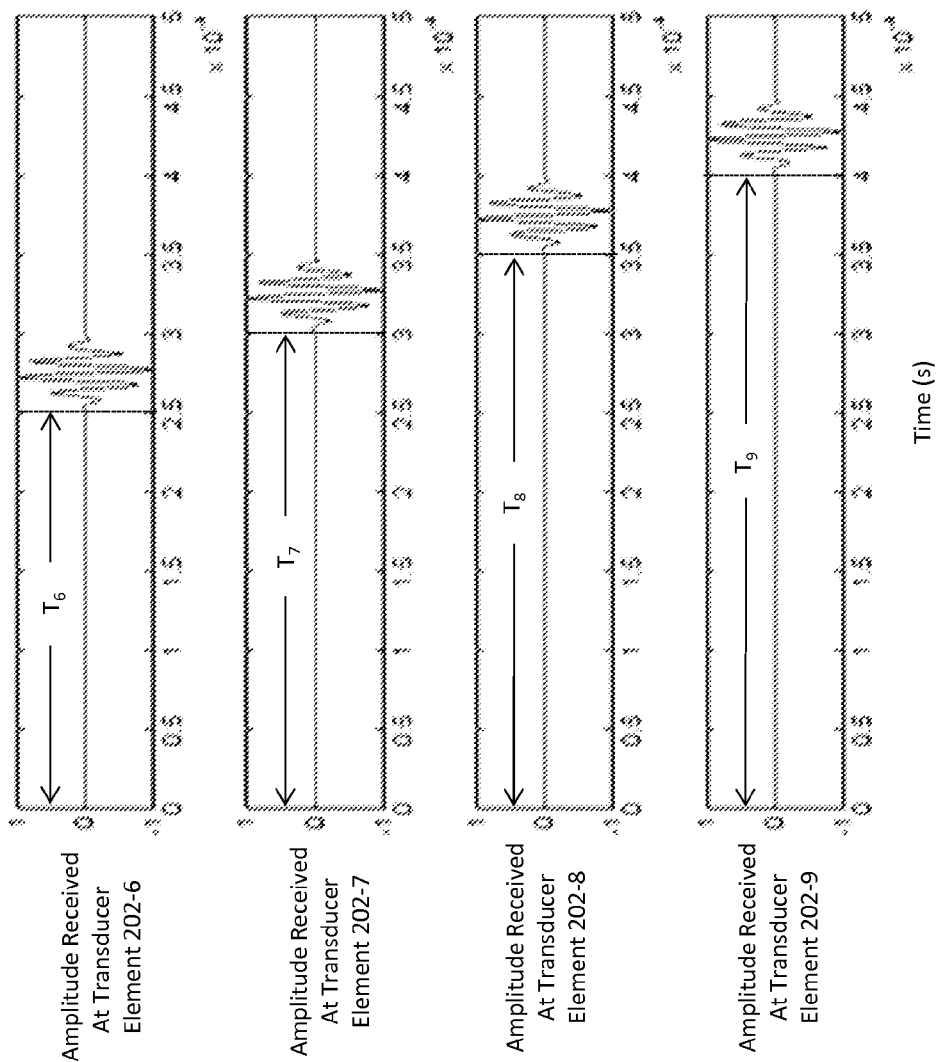
FIG. 6 illustrates arrival time differences of acoustic emission signals received as a result of a damage/impact in accordance with FIG. 5.

Sample received waveforms in which the trigger even was the release of the ultrasonic energy from the defect and received at transducer elements 202-6:202-9 are illustrated in FIG. 6. If the trigger event was not the release of the ultrasonic energy from the defect, then the initial time would start at some value of delta t and not 0. The arrival times $T_6$-$T_9$ are identified in FIG. 6 based on an assumption that delta t is zero.

Figure 7:
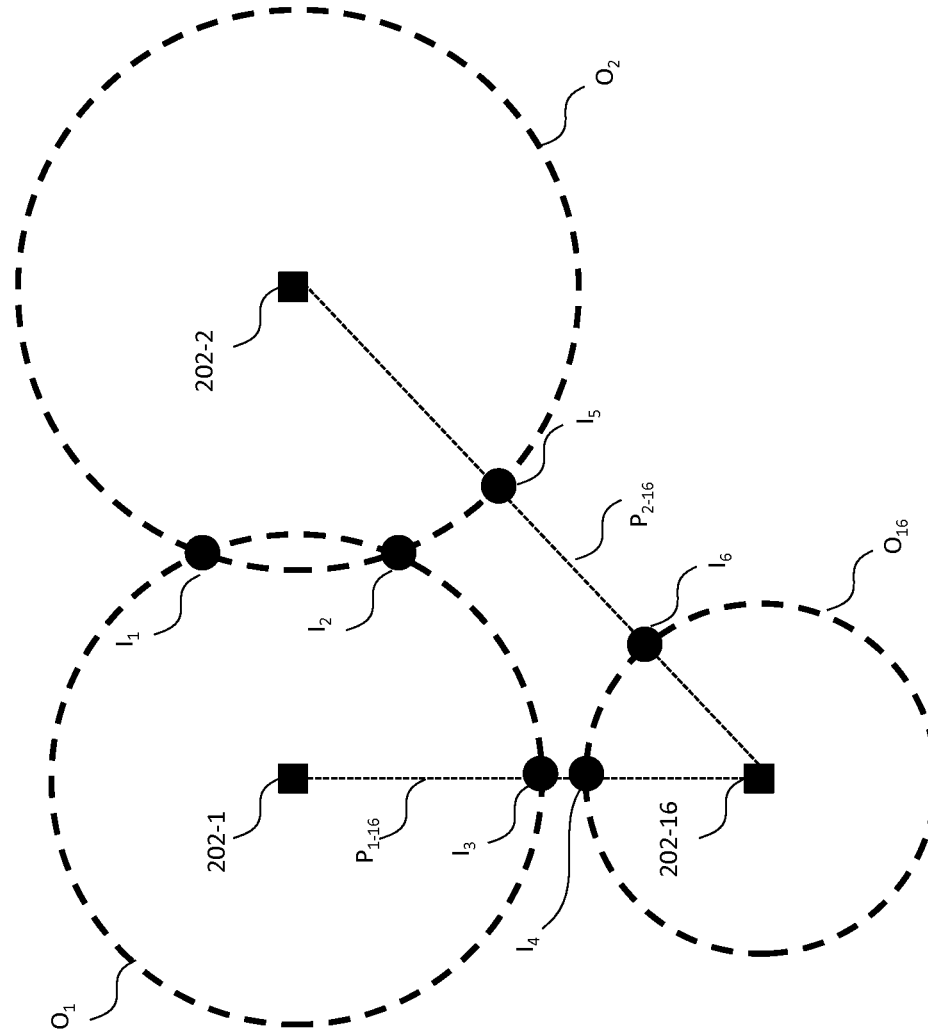
FIG. 7 illustrates a process for determining a location of a source of an acoustic emission in a material having unknown properties.

In order to locate defect/impact locations, an iterative process is performed using trial values of delta t and wave speed, C, for the acoustic emissions to determine the defect location in the material 100 even when the material properties are not available. If material 100 is isotropic, the iterative computations can be carried out based on the arrival time of the acoustic emission signals received by transducer elements 202. The arrival time of the acoustic emission signals received by any three transducer elements is used with the estimated wave speed, C, and delta t values to predict the acoustic emission source location. FIG. 7 illustrates an example in which transducer elements 202-1, 202-2, and 202-16 are used. Three circles are plotted using the locations of the three transducer elements as the centers of the circles. The circles have a radius, $R_n$, which is determined according to the following equation:

$$R_n = (\Delta t + T_n) * C \qquad \text{Eq. 19}$$

Where,
$T_n$ is the arrival time of a signal at the $n^{th}$ transducer element, and
C is the wave velocity of the signal.

As shown in FIG. 7, the circles $O_1$ and $O_2$ respectively plotted around transducer elements 202-1 and 202-2 intersect at points $I_1$ and $I_2$. The intersection points are possible acoustic source locations for the estimated wave speed, C, and delta t values. If the C and delta t values are correct, one of the intersection points of the pair of circles should coincide with one intersection point of another circle pair.

If the trial values of C and delta t are not correct, then the values of C and delta t are updated to match the actual values of C and delta t. To update the C and delta t values, special treatment is applied to the circles that do not intersect. Lines are plotted between the transducer element pairs that do not have intersecting circles. For example, line $P_{1-16}$ is drawn between transducer elements 202-1 and 202-16, and line $P_{2-16}$ is drawn between transducer elements 202-2 and 202-16 since the circles $O_2$ and $O_{16}$ respectively surrounding transducer elements 202-2 and 202-16 do not intersect, nor do circles $O_1$ and $O_{16}$ surrounding transducer elements 202-1 and 202-16 intersect. Line $P_{2-16}$ and circles $O_2$ and $O_{16}$ respectively intersect at points $I_3$ and $I_4$, and line $P_{1-16}$ and circles $O_1$ and $O_{16}$ intersect at points $I_5$ and $I_6$. A calculation is performed to determine which intersection points $I_1$-$I_6$ provide a triangle having the smallest perimeter utilizing at least one intersection point for each of the intersection point pairs, i.e., intersection point pairs $I_1$ and $I_2$, $I_3$ and $I_4$, and $I_5$ and $I_6$. In the example illustrated in FIG. 7, points $I_3$, $I_4$, and $I_5$ yield a triangle having the smallest perimeter. This calculation may be applied to any three transducer elements in the acoustic emission transducer element network.

Iterative calculations can be carried out by perturbations of C and delta t until the summation of the minimum distance for each possible combination of three transducer elements is determined. In some embodiments, the iterative process is a genetic algorithm-based method in which the fitness function is defined by:

$$f = 1/(\Sigma D_m) \qquad \text{Eq. 20}$$

Where,
$D_m$ is the smallest perimeter found for the $m^{th}$ combination of three transducer elements as described above.

The summation is over all possible combinations of three transducer elements, and the genetic algorithm-based calculations stop when the fitness function reaches a defined threshold value, which may be stored in a computer readable storage medium. The values of C and delta t at the stop point of the iterative process is the approximate value of the wave velocity and the first arrival time of the acoustic emission at the transducer element network. The region enclosed by the stop of the iterative calculation identifies the source location of the acoustic emission. Once identified, a location, size, and shape of the defect 104 may be stored in a computer readable storage medium 210, 212. Additionally, a rendering of the defect 104 created by the processor 206 may be displayed to a user of the control and processing device 204 on the display 224 as will be understood by one skilled in the art.

Figure 8A:
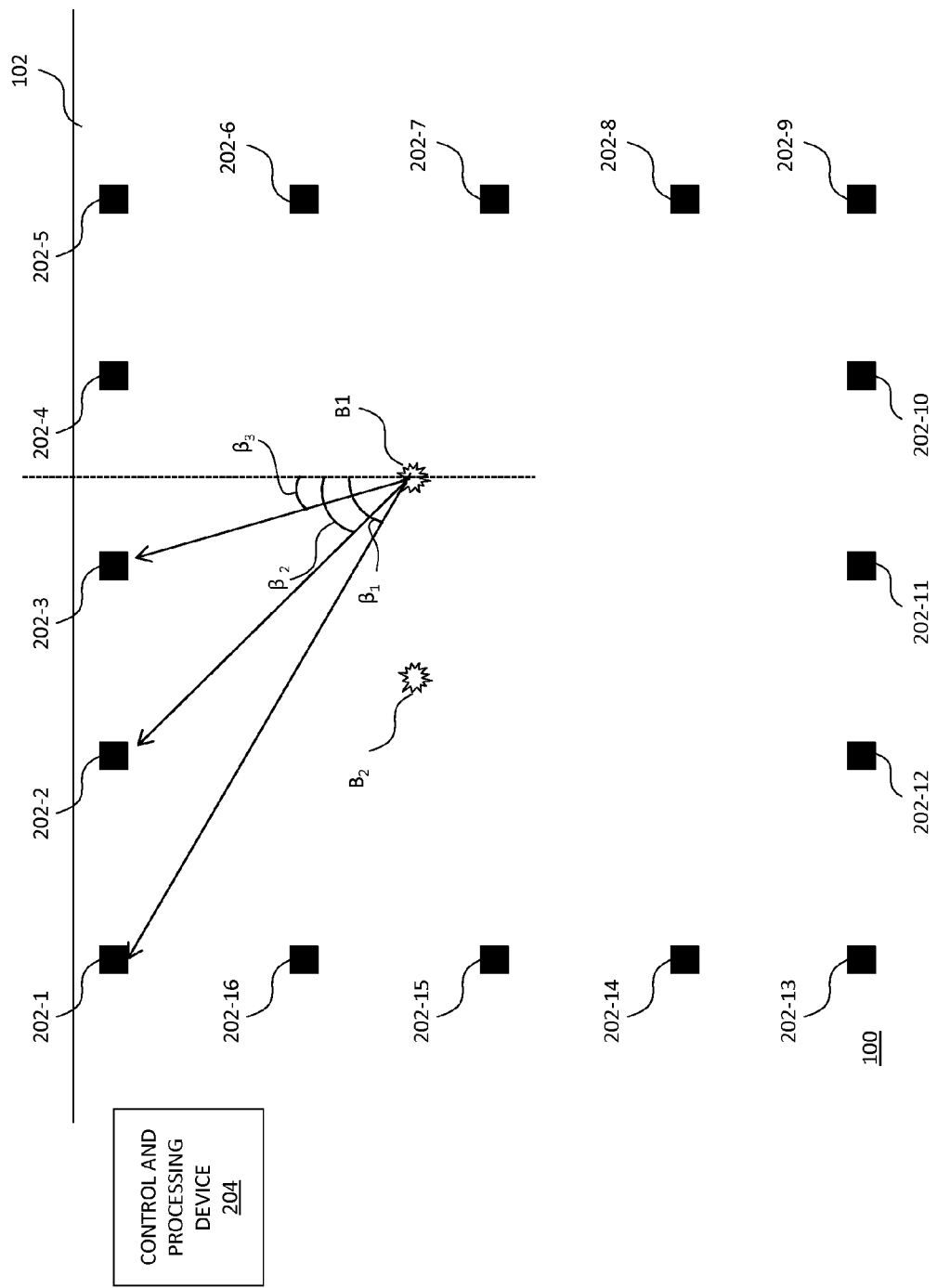
FIG. 8A illustrates an example of a process for calibrating the acoustic emission detection system illustrated in FIG. 7.

If material 100 is anisotropic material, a calibration process using pensile breaks is performed for the establishment of the energy velocity profile with respect to different wave energy propagation directions. FIG. 8A illustrates an example of the calibration process. Pensile breaks $B_1$ and $B_2$ are applied to material 100 at known locations. As illustrated in FIG. 8A, the angles $\beta_1$, $\beta_2$, and $\beta_3$ of the wave paths between the pensile break $B_1$, $B_2$ and the transducer elements to a reference direction, which in the illustrated example is an axis orthogonal to an axis defined by transducer elements 202-1:202-3, are known. The wave energy velocities as a function of the angles with respect to the reference direction can be obtained based on the arrival time of the acoustic emission signals generated by the pensile breaks and the corresponding distances between the pensile break positions and the transducer elements. An interpolation on the energy velocity profile is applied for the completeness of the energy velocity profile $C(\beta)$, $0° = <\beta<360°$. A similar iterative computation process to the process described above for the isotropic case is performed in which the trial wave velocity C is replaced by $C(\beta)$. Additionally, instead of using circles to find intersection points, non-circle curves are plotted using the acoustic emission transducer element positions as the origins of polar coordinate systems and based on the equation as follow:

$$R_n(\beta) = (dt + T_n) * C(\beta), 0° = <\beta<360° \qquad \text{Eq. 21}$$

Figure 8C:
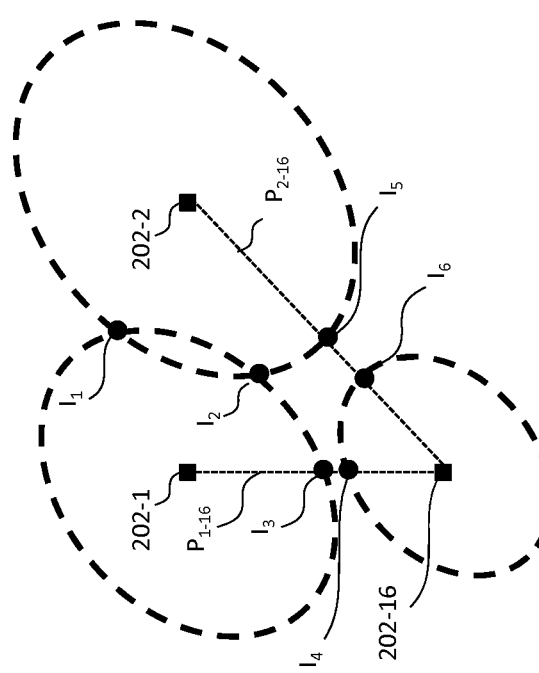
FIG. 8C illustrates another example of determining a location of a source of an acoustic emission in a material having an unknown property.
Figure 8B:
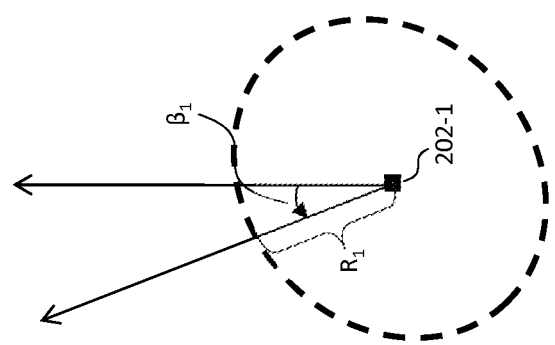
FIG. 8B illustrates an example of a curve being plotted in accordance with the process for calibrating the acoustic emission detection system illustrated in FIG. 8A.

FIG. 8B illustrates an example of a curve plotted based on Equation 21 for transducer element 202-1 in FIG. 8A. The intersection points $I_1$-$I_6$ among the curves of transducer elements 202-1, 202-2, and 202-16 are illustrated in FIG. 8C. In this case, intersection points $I_2$, $I_3$, and $I_5$ provide a triangle having the smallest perimeter for transducer elements 202-1, 202-2, and 202-16 using at least one intersection point from each intersection point pair. The iterative calculation process minimizes the overall summation of the minimum distance found for every possible combinations of three transducer elements. The example generic algorithm based iterative calculations for the isotropic materials uses the same fitness function set forth above by Equation 20, and the value of delta t is the only input parameter subject to perturbation in the generic algorithm calculations. If necessary, perturbations can also be applied to the interpolation of the energy velocity profile such that both delta t and $C(\beta)$ are input parameters for the genetic algorithm calculations. The location of the acoustic emission source can therefore be determined for anisotropic material 100 even when the material properties and wave speeds are unknown.

In an example embodiment of the acoustic emission system, there are no specific limitations on the shape of the transducer element network. Circular, rectangular, elliptical, or even arbitrary transducer element network consisting with more than three transducer elements are applicable. Faster and more accurate damage/impact location process can be achieved if more transducer elements are used.

Figure 9A:
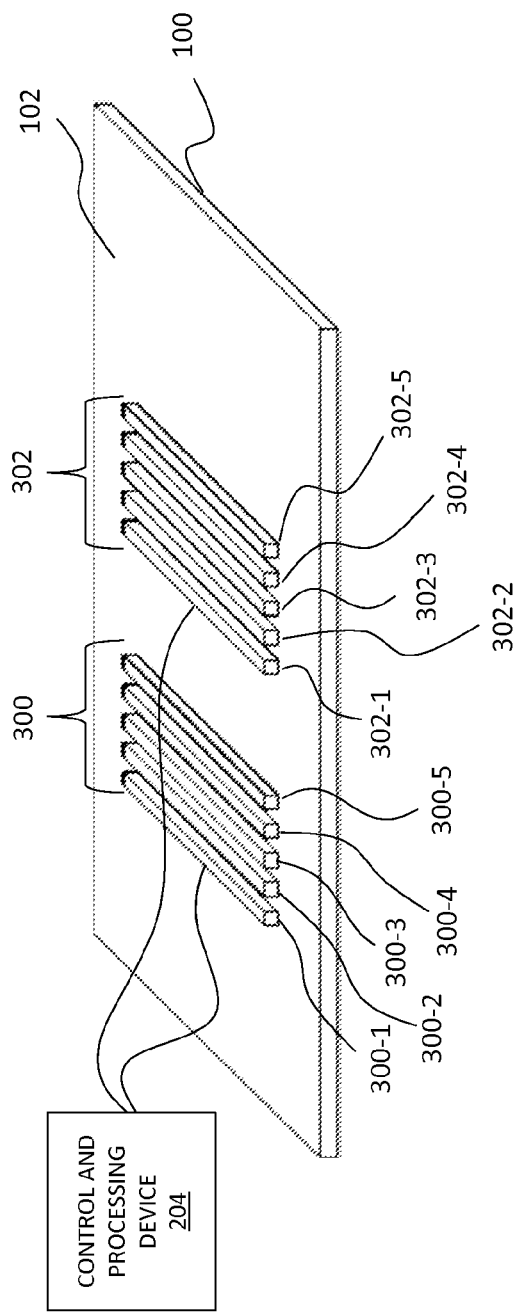
FIGS. 9A and 9B illustrate one example of a time delayed comb type transducer.
Figure 9B:
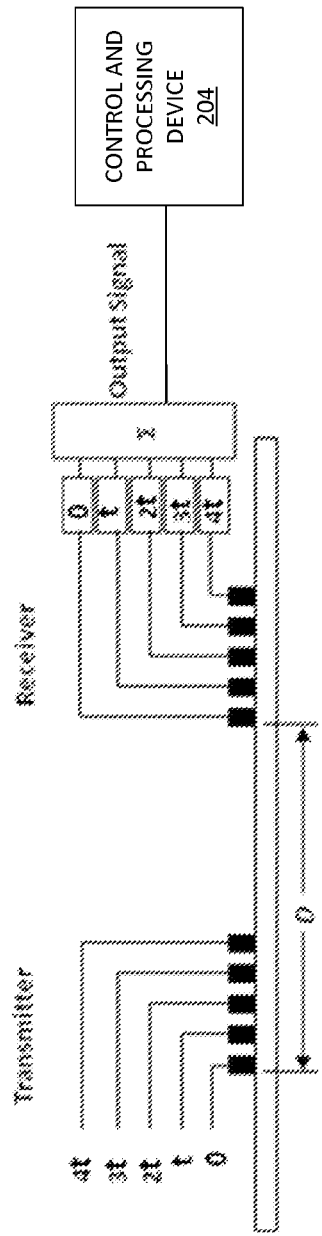
Figure 10A:
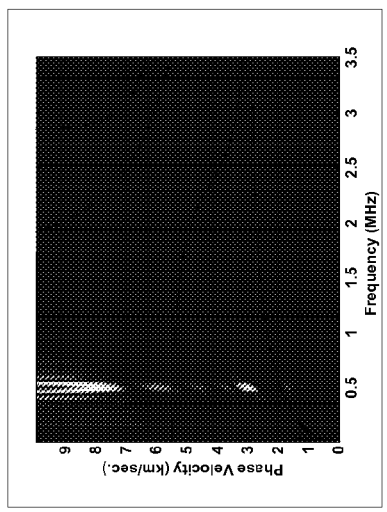
FIGS. 10A-10D are examples of guided wave excitation spectrums of the comb type transducer when different time delays are applied.
Figure 10B:
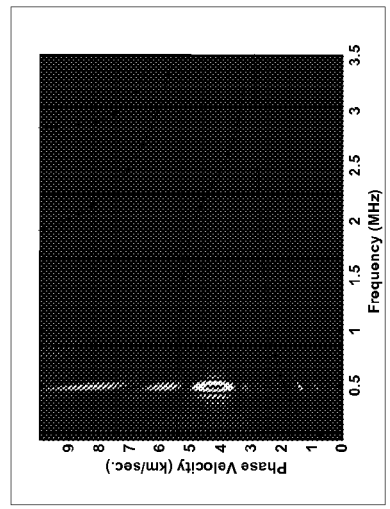
Figure 10C:
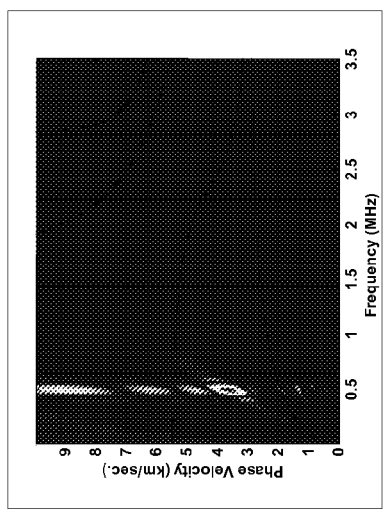
Figure 10D:
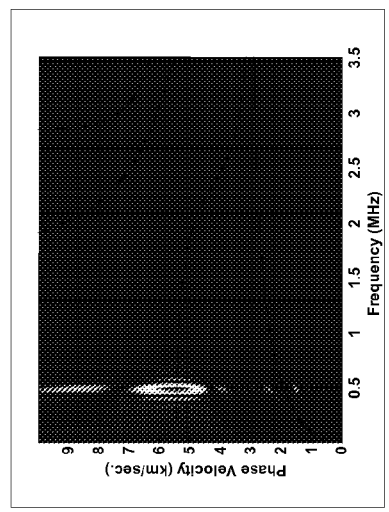

FIGS. 9A and 9B illustrate an example embodiment of a time-delay comb-type transducer for guided wave inspection of materials having unknown material properties and/or thicknesses. The system may be used to inspect materials having shapes that have a defined boundary forming a waveguide such as, for example, plates, beams, or the like. As shown in FIGS. 9A and 9B, an array 300 of five transmitters 300-1:300-5 and an array 302 of five receivers 302-1:302-5 are positioned on a surface 102 of a plate 100. Prior to the defect inspection, time delay and frequency tuning are applied to the comb transducer elements to generate guided wave signals between the transmitter elements 300 and the receiver elements 302. Referring to FIG. 9B, the time delays applied to the transmitting transducer elements 300 are also applied to the transmission signals received by the receiving transducer elements 302. The time delayed received signals are then summed together to general a received signal. The amplitudes of the received guided wave signals vary with the time delays. Optimal time delays and frequency can be found by searching the maximum guided wave amplitude. The optimal time delays and frequency yield the maximum guided wave amplitude because the excitation zone of the time delay comb transducer coincides with a guided wave mode in the phase velocity-frequency domain. The guided wave mode can thus be selected and used for defect detection purposes. The group velocity of the selected guided wave mode can be calculated from the distance between the transmitter and receiver elements. Therefore, the optimal time delays and frequency can be used with the time delay comb transducer to detect as well as to locate possible defects in the plate. There is no need to calculate guided wave dispersion curves for the defect inspection process. In an example embodiment of the comb transducer for inspecting isotropic plates, a three or more transmitting transducer elements are implemented and one or more receiving transducer elements are implemented. Better guided wave mode selection can be achieved when more elements are used, however, the length of the main band signals may be increased.

Referring to FIGS. 10A-10D, the excitation spectrum of the time delay comb transducer in the phase velocity-frequency domain can be varied by the employment of different time delays for the transmitter-receiver pairs of the comb transducer. The time delays for the transmitters 300 may be applied in real time or in a synthetic manner. In the synthetic approach, only one transmitter element is activated at a time for guided wave transmission. The time delays are applied to the signals that are received when different transmitter elements are activated. The final signals are the summations of the time delayed received signals.

Example phase velocity dispersion curves for a 1 mm thick aluminum plate are overlapped with the excitation spectrums in FIGS. 10A-10D. If the highlighted excitation zone of the comb transducer coincides with a guided wave mode in the dispersion curves, the guided wave mode can be effectively selected by the comb transducer. Referring to FIGS. 11A-11D, the experimental guided wave signals that respectively correspond to the excitation spectrums shown in FIGS. 10A-10D demonstrate the mode selection capability of the time delay comb type transducer.

Figure 12:
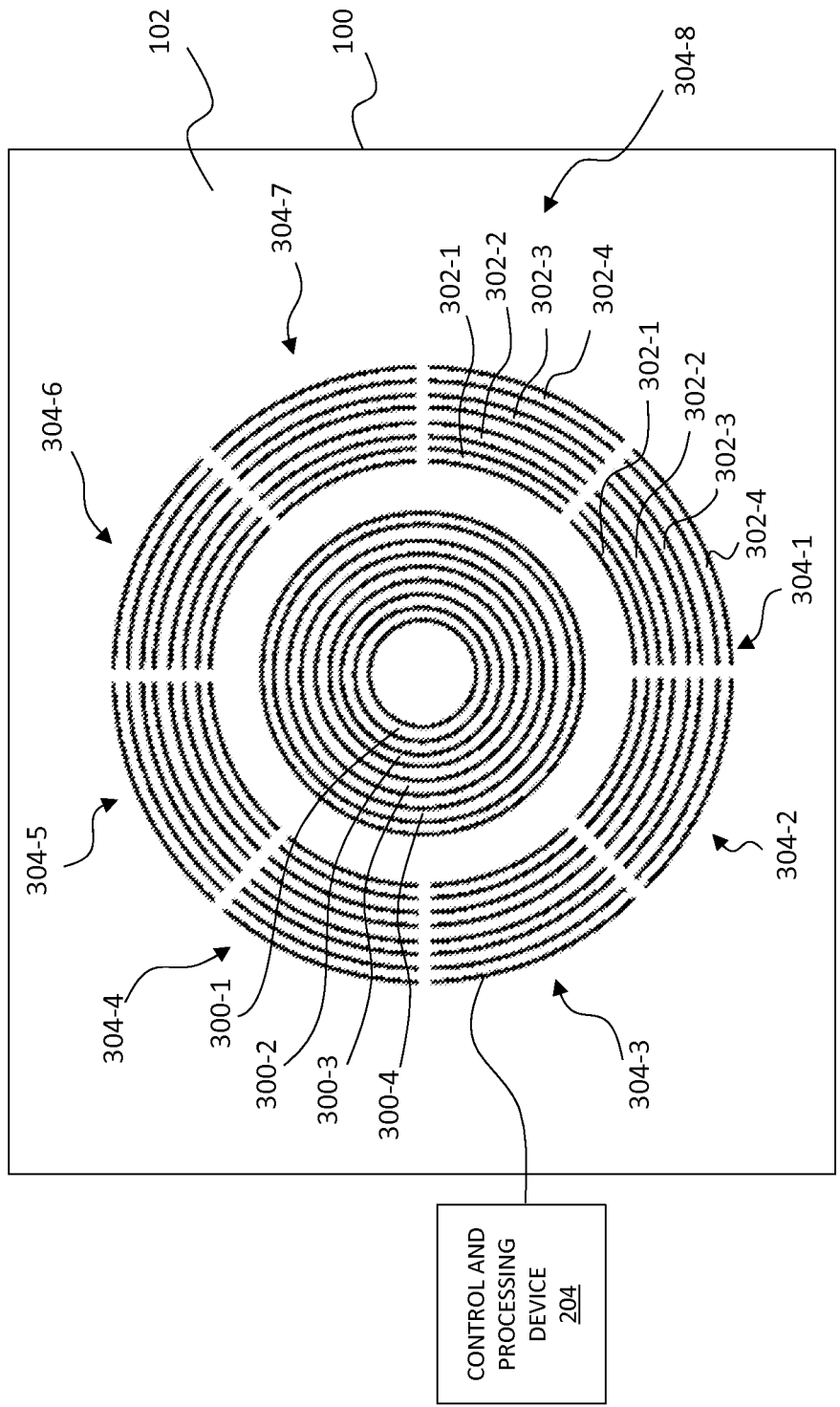
FIG. 12 is a plan view of one example of a circular transducer arrangement for inspecting a material having unknown properties.
Figure 13:
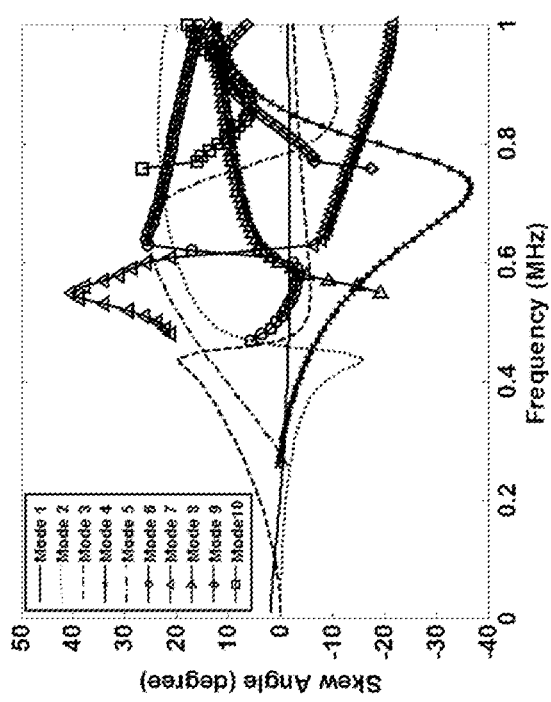
FIG. 13 shows an example skew angle dispersion curves of a composite plate.

For anisotropic plates including fiber reinforced composite plates, guided wave skew effects may occur due to material anisotropy. FIG. 12 illustrates an example embodiment of a circular comb-type transducer that can be used to inspect anisotropic plates. As shown in FIG. 12, a plurality of spaced apart transmitters 300-1:300-4 are arranged in a circular pattern and are surrounded by a plurality of spaced apart receiver segments 304-1:304-8. Each of the receiver segments 304-1:304-8 includes a plurality of spaced apart receivers, e.g., receivers 302-1:302-4. Each of the transmitters 300 and receivers 302 may be coupled to a control and processing device 204 as described above. Different guided wave modes have different skew angles due to the material anisotropy. The skew angles are also different at different frequencies for the same guided wave mode. FIG. 13 illustrates the skew angle dispersion curves for different wave modes at different frequencies. When the material properties and plate thickness are unknown, the skew angle dispersion curves are not available. Defect inspection can be performed without the skew angle dispersion curves using the circular comb transducer illustrated in FIG. 12. Prior to the defect inspection, a time delay and frequency tuning is applied to the circular transmitters 300. For each time delay and frequency combination, all of the segment annular arrays surrounding the transmitters are used to receive guided wave signals individually. Due to the wave skew effects, although the transmitters 300 act as an axisymmetric transmitter, the signals received by the different receivers 302 are different. For each annular segment 304-1:304-8, optimal time delays and frequencies may be found when the maximum amplitude of the received signal is achieved. With the optimal time delays, the direction from the center transmitter to the corresponding annular segment 304-1:304-8 can be inspected. The group velocity of the selected guided wave mode and frequency can be determined based on the arrival time of the directly received guided wave signal and the distance between the center transmitter 300 and the receiver in the annular segment. Different inspection directions may be covered by different annular segments with different time delays and frequencies.

In some embodiments, three transmitters are implemented with each annular segment 304-1:304-8 having a corresponding number of receivers 302. However, more transmitters 300 and receivers 302 per annular receiving segment 304 may be implemented for better circumferential resolution. At the same time, more channels are implemented for recording the guided wave signals using the annular segment 304.

The disclosed systems and methods advantageously enable the inspection of anisotropic and isotropic materials when the properties of the material are not known. Additionally, the disclosed systems and methods enable the identification of defects in materials and the location of defects to be calculated.

The disclosed system and method may be embodied in the form of computer-implemented processes and apparatus for practicing those processes. The disclosed system and method may also be embodied in the form of computer program code embodied in tangible machine readable storage media, such as random access memory (RAM), floppy diskettes, read only memories (ROMs), CD-ROMs, hard disk drives, flash memories, or any other machine-readable storage medium, wherein, when the computer program code is loaded into and executed by a computer, the computer becomes an apparatus for practicing the method. The system and method may also be embodied in the form of computer program code loaded into and/or executed by a computer, such that, when the computer program code is loaded into and executed by a computer, the computer becomes an apparatus for practicing the method. When implemented on a general-purpose processor, the computer program code segments configure the processor to create specific logic circuits. The invention may alternatively be embodied in a digital signal processor formed of application specific integrated circuits for performing a method according to the principles described herein.

Although the disclosed systems and methods have been described in terms of exemplary embodiments, they are not limited thereto. Rather, the appended claims should be construed broadly, to include other variants and embodiments of the systems and methods, which may be made by those skilled in the art without departing from the scope and range of equivalents.

What is claimed is:

1. An inspection system, comprising:
a plurality of spaced apart transmitting transducer elements for coupling to a surface of a material defining a transmission medium, each of the transmitting transducer elements configured to transmit ultrasonic guided wave signals through the transmission medium;
a receiving transducer element for coupling to the surface of the material at a distance from the plurality of transmitting transducer elements, the receiving transducer configured to receive ultrasonic guided wave signals through the transmission medium; and
a control and processing device in signal communication with each of the transducer elements, the control and processing device including:
a computer readable storage medium configured to store a plurality of time delays for applying to each of the transducer elements; and
a processor in signal communication with the computer readable storage medium, the processor configured to apply the time delays and a driving frequency to the transmitting transducer elements,
determine a respective time delay and frequency for each of the transmitting transducer elements that provides a maximum amplitude in a guided wave signal received at the receiving transducer element without using any guided wave dispersion curves,
activate each of the plurality of transmitting transducer elements in accordance with the determined time delay and frequency to transmit an inspection signal through the transmission medium, and
determine a location of a defect in the material based on a velocity of the inspection signal received at the receiving transducer element.

2. The inspection system of claim 1, wherein the transmitting transducer elements are disposed on the surface of the material in a linear array.

3. The inspection system of claim 1, wherein the receiving transducer element further comprises a plurality of receiving transducer elements disposed on the surface of the material in a linear array.

4. The inspection system of claim 1, wherein the transmitting transducer elements are disposed in a concentric circular array.

5. The inspection system of claim 4, wherein the receiving transducer element further comprises a plurality of receiving transducer elements disposed in a concentric circular array surrounding the transmitting transducer elements.

6. An inspection method, comprising:
driving each of a plurality of spaced apart transmitting transducer elements with a respective time delay and a respective frequency such that each of the transmitting transducer elements transmits an ultrasonic guided wave through a transmission medium defined by a material;
receiving the ultrasonic guided waves at a receiving transducer element disposed on the surface of the material at a distance from the plurality of transmitting transducer elements;
determining, by a processor, a respective time delay and a respective frequency for each of the transmitting transducer elements that provides a maximum amplitude in a guided wave signal received at the receiving transducer element without using any guided wave dispersion curves;
activating each of the plurality of transmitting transducer elements in accordance with the determined time delays and frequencies to transmit inspection signals through the transmission medium, and
determining, by a processor, a location of a defect in the material based on velocities of the inspection signals received at the receiving transducer element.

7. The inspection method of claim 6, wherein the transmitting transducer elements are disposed on the surface of the material in a linear array.

8. The inspection method of claim 6, wherein the receiving transducer element further includes a plurality of receiving transducer elements are disposed on the surface of the material in a linear array.

9. The inspection method of claim 6, wherein the transmitting transducer elements are disposed in a concentric circular array.

10. The inspection method of claim 9, wherein the receiving transducer element includes a plurality of receiving transducer elements are disposed in a concentric circular array surrounding the transmitting transducer elements.

11. The inspection method of claim 6, further comprising:
storing the location of the defect in a computer readable storage medium.

12. The inspection method of claim 6, further comprising:
displaying the location of the defect to a user on a display device.

13. A non-transitory computer readable storage medium encoded with program code, wherein when the program code is executed by a processor, the processor performs a method, the method comprising:
driving each of a plurality of spaced apart transmitting transducer elements with a respective time delay and a respective frequency such that each of the transmitting transducer elements transmits an ultrasonic guided wave through a transmission medium defined by a material;
receiving the ultrasonic guided waves at a receiving transducer element disposed on the surface of the material at a distance from the transmitting transducer elements;
determining a respective time delay and a respective frequency for each of the transmitting transducer elements that provides a maximum amplitude in a guided wave signal received at the receiving transducer element without using any guided wave dispersion curves;
activating each of the plurality of transmitting transducer elements in accordance with the determined time delays and frequencies to transmit inspection signals through the transmission medium, and
determining a location of a defect in the material based on velocities of the inspection signals received at the receiving transducer element.

14. The non-transitory computer readable storage medium of claim 13, wherein the transmitting transducer elements are disposed on the surface of the material in a linear array.

15. The non-transitory computer readable storage medium of claim 13, wherein the receiving transducer element includes a plurality of receiving transducer elements are disposed on the surface of the material in a linear array.

16. The non-transitory computer readable storage medium of claim 13, wherein the transmitting transducer elements are disposed in a concentric circular array.

17. The non-transitory computer readable storage medium of claim 16, wherein the receiving transducer element includes a plurality of receiving transducer elements are disposed in a concentric circular array surrounding the transmitting transducer elements.

* * * * *